US006860158B2

(12) United States Patent
Bitto et al.

(10) Patent No.: US 6,860,158 B2
(45) Date of Patent: Mar. 1, 2005

(54) CORIOLIS MASS FLOW RATE/DENSITY/ VISCOY SENSOR WITH TWO BENT MEASURING TUBES

(75) Inventors: Ennio Bitto, Aesch (CH); Christian Schütze, Basel (CH); Ole Koudal, Baden (CH)

(73) Assignee: Endress + Hauser Flowtec AG, Reinach (CH)

( * ) Notice: Subject to any disclaimer, the term of this patent is extended or adjusted under 35 U.S.C. 154(b) by 0 days.

(21) Appl. No.: 10/640,360

(22) Filed: Aug. 13, 2003

(65) Prior Publication Data

US 2004/0045369 A1 Mar. 11, 2004

Related U.S. Application Data

(63) Continuation of application No. 09/832,751, filed on Apr. 11, 2001, now Pat. No. 6,711,958.
(60) Provisional application No. 60/205,983, filed on May 19, 2000.

(30) Foreign Application Priority Data

May 12, 2000 (EP) ............................................ 00110091

(51) Int. Cl.[7] .............................................. G01F 1/78
(52) U.S. Cl. ................................................ 73/861.355
(58) Field of Search ...................... 73/861.355, 861.357, 73/861.356, 861.354

(56) References Cited

U.S. PATENT DOCUMENTS

| 4,127,028 A | 11/1978 | Cox et al. |
| 4,187,721 A | 2/1980 | Smith |

(List continued on next page.)

FOREIGN PATENT DOCUMENTS

| EP | 0 553 939 | 8/1986 |
| EP | 1 001 254 A1 | 5/2000 |
| EP | 1 001 254 | 5/2000 |
| JP | 56125622 | 10/1981 |
| JP | 11351939 | 12/1999 |
| JP | 2000046613 | 2/2000 |
| WO | WO 99/63309 | 12/1999 |
| WO | WO 00/57141 | 9/2000 |

*Primary Examiner*—Edward Lefkowitz
*Assistant Examiner*—Jewel V. Thompson
(74) *Attorney, Agent, or Firm*—Bose McKinney & Evans LLP

(57) ABSTRACT

This sensor (10) generates accurate measuring results, for example with an error in the order of 0.5% of the measuring value, hat has mimimized production costs as well as a shorter overall length compared to that of conventional sensors. The sensor has two parallel V shaped measuring tubes (1, 2) each being of one-piece construction. Each tube has a straight inlet portion (11, 21), a straight outlet portion (12, 22), an inlet bend (13, 23) connected with the inlet portion, an outlet bend (14, 24) connected with the outlet portion, a straight tube portion (15, 25) connected with the inlet bend, a straight tube portion (16, 26) connected with the outlet bend, and a vertex bend (17, 27) connected with the first and second straight tube portions. The inlet portions (11, 21) are fixed in an inlet manifold (18) and the outlet portions in an outlet manifold (19); the manifolds (18, 19) are mounted in a support frame (30) which forms part of a housing (3). An excitation arrangement (6) causes the measuring tubes (1, 2) to vibrate as a tuning fork. Interspaced sensor elements (7, 8) are fixed to the measuring tubes. Mounted in the support frame (30) is a feedthrough (37) for a printed-circuit board (96) having conducting tracks (97) to which leads (63, 64, 73, 74, 83, 84) of the excitation system (6) and of the sensor elements (7, 8) are connected.

61 Claims, 3 Drawing Sheets

U.S. PATENT DOCUMENTS

| | | |
|---|---|---|
| 4,622,858 A | 11/1986 | Mizerak |
| 4,738,143 A | 4/1988 | Cage et al. |
| 4,781,069 A | 11/1988 | Mitzner |
| 4,801,897 A | 1/1989 | Flecken |
| 4,852,410 A | 8/1989 | Corwon et al. |
| 4,876,898 A | 10/1989 | Cage et al. |
| 5,090,253 A | 2/1992 | Kolpak |
| 5,301,557 A | 4/1994 | Cage et al. |
| 5,307,689 A | 5/1994 | Nishiyama et al. |
| 5,349,872 A | 9/1994 | Kalotay et al. |
| 5,663,509 A | 9/1997 | Lew et al. |
| 5,796,011 A | 8/1998 | Keita et al. |
| 6,006,609 A | 12/1999 | Drahm et al. |
| 6,308,580 B1 | 10/2001 | Crisfield et al. |
| 6,711,958 B2 * | 3/2004 | Bitto et al. ............ 73/861.355 |

* cited by examiner

CORIOLIS MASS FLOW RATE/DENSITY/VISCOY SENSOR WITH TWO BENT MEASURING TUBES

RELATED APPLICATIONS

This application is a continuation of application Ser. No. 09/832,751 filed Apr. 11, 2001, now U.S. Pat. No. 6,711,958, the disclosure of which is hereby expressly incorporated by reference, which claims the benefit of U.S. Provisional Application Ser. No. 60/205,983, filed May 19, 2000, the disclosure of which is hereby expressly incorporated by reference, and the benefit of European Patent Application 00110091.6, filed May 12, 2000, the disclosure of which is hereby expressly incorporated by reference.

BACKGROUND AND SUMMARY OF THE INVENTION

This invention relates to a mass flow rate/density/viscosity sensor working on the Coriolis principle—hereinafter referred to as a Coriolis sensor for short—and comprising two bent measuring tubes.

With such Coriolis sensors, whose measuring tubes, as is well known, are set into vibration, particularly into flexural vibration with or without superposed torsional vibration, it is possible to measure not only the instantaneous mass flow rate of a fluid flowing in a pipe, but also the density of the fluid via the instantaneous vibration frequency of the measuring tubes and the viscosity of the fluid via the power required to maintain the vibrations of the tubes.

Since the temperature of the fluid is not constant during operation of the Coriolis sensor, and the density of the fluid, as is well known, is temperature-dependent, the Coriolis sensor is commonly provided with at least one temperature sensor for measuring the temperature of the fluid. For all those measurements, the Coriolis sensor is connected into the pipe in a pressure-tight manner and generally permanently, for example via flanges.

U.S. Pat. No. 4,187,721 discloses a Coriolis mass flow rate/density sensor designed to be installed in a pipe through which a fluid flows at least temporarily, and comprising:
 a single, U-shaped measuring tube bent in one plane symmetrically with respect to an axis of symmetry, which
  is of one-piece construction and
  has a straight inlet portion fixed in a support angle,
  a straight outlet portion fixed in the support angle,
  an offset inlet transition portion connected with the inlet portion,
  an offset outlet transition portion connected with the outlet portion,
  a first bent portion connected with the inlet transition portion,
  a second bent portion connected with the outlet transition portion,
  a straight base portion connecting the first and second bent portions;
 an excitation system
  which in operation causes the measuring tube together with an exciter carrier to vibrate as a tuning fork,
  a first portion of which is fixed to the base portion in the area of the axis of symmetry, and
  a second portion of which is fixed to the exciter carrier;
 a first optical sensor,
  a first portion of which is fixed to the measuring tube at a location
   where the inlet transition portion passes into the first bent portion, and
  a second portion of which is fixed to the support angle; and
 a second optical sensor,
  a first portion of which is fixed to the measuring tube at a location
   where the outlet transition portion passes into the second bent portion, and
  a second portion of which is fixed to the support angle.

JP-A 56-125 622 discloses a Coriolis mass flow rate sensor designed to be installed in a pipe through which a fluid flows at least temporarily, and comprising:
 an omega-shaped measuring tube bent in one plane symmetrically with respect to an axis of symmetry which
  is of one-piece construction and
  has a straight inlet portion with an inlet axis lying in said plane,
  a straight outlet portion with an outlet axis aligned with the inlet axis,
  an S-shaped inlet bend connected with the inlet portion,
  an S-shaped outlet bend connected with the outlet portion, and
  a vertex bend connecting the inlet and outlet bends;
 an excitation system
  which in operation causes the measuring tube together with an exciter carrier to vibrate as a tuning fork,
  a first portion of which is fixed to the vertex bend in the area of the axis of symmetry, and
  a second portion of which is fixed to the exciter carrier;
 a bar-shaped sensor carrier
  which extends perpendicular to the axis of symmetry,
  a first end of which is fixed to the measuring tube at a location where the inlet bend passes into the vertex bend, and
  a second end of which is fixed to the measuring tube at a location where the outlet bend passes into the vertex bend; and
 a strain-gage bridge disposed as a sensor arrangement on the sensor carrier.

U.S. Pat. No. 4,127,028 discloses a Coriolis mass flow rate sensor designed to be installed in a-pipe through which a fluid flows at least temporarily, and comprising:
 a first U-shaped measuring tube bent in a first plane symmetrically with respect to a first axis of symmetry;
 a second U-shaped measuring tube bent in a second plane symmetrically with respect to a second axis of symmetry,
  which measuring tubes are arranged parallel to each other, are of one-piece construction, and are connected in series in terms of fluid flow, and
  each of which measuring tubes has
   a straight inlet portion,
   a straight outlet portion,
   an S-shaped inlet bend connected with the inlet portion,
   an S-shaped outlet bend connected with the outlet portion,
   a first straight tube portion connected with the inlet bend,
   a second straight tube portion connected with the outlet bend, and
   a semicircular base bend connected with the first and second straight tube portions,
    which inlet and outlet portions extend through a fixed member, with the distance between the inlet and outlet portions of each measuring tube being less than the distance between the first and second straight tube portions of the respective measuring tube;

an excitation system
  which during operation causes the measuring tubes to vibrate as a tuning fork,
  a first portion of which is fixed to the semicircular base bend of the first measuring tube in the area of the axis of symmetry of the first measuring tube, and
  a second portion of which is fixed to the semicircular base bend of the second measuring tube in the area of the axis of symmetry of the second measuring tube;

a first optical sensor,
  a first portion of which is fixed to the first measuring tube and a second portion of which is fixed to the second measuring tube at respective locations where the respective first straight tube portion passes into the respective semicircular base bend; and a second optical sensor,
  a first portion of which is fixed to the first measuring tube and a second portion of which is fixed to the second measuring tube at respective locations where the respective second straight tube portion passes into the respective semicircular base bend.

U.S. Pat. No. 4,622,858 discloses a Coriolis mass flow rate sensor designed to be installed in a pipe through which a fluid flows at least temporarily, and comprising:

a first straight measuring tube;
a second straight measuring tube,
  which measuring tubes are arranged parallel to each other,
  are of one-piece construction, and
  are connected in parallel in terms of fluid flow by means of an inlet manifold and an outlet manifold;

a driving mechanism
  which in operation vibrates the measuring tubes as a tuning fork,
  a first portion of which is fixed to the first measuring tube midway between the inlet manifold and the outlet manifold, and
  a second portion of which is fixed to the second measuring tube midway between the inlet manifold and the outlet manifold;

a first electrodynamic sensor,
  a first portion of which is fixed to the first measuring tube midway between the driving mechanism and the inlet manifold, and a second portion of which is fixed to the second measuring tube midway between the driving mechanism and the inlet manifold; and a second electrodynamic sensor,
  a first portion of which is fixed to the first measuring tube midway between the driving mechanism and the outlet manifold, and a second portion of which is fixed to the second measuring tube midway between the driving mechanism and the outlet manifold.

U.S. Pat. No. 6,006,609 discloses a Coriolis mass flow rate/density/viscosity sensor designed to be installed in a pipe through which a fluid flows at least temporarily, and comprising:

a single straight measuring tube of one-piece construction which is provided with a cantilever at its midpoint, and an inlet end and an outlet end of which are mounted in a support frame which is disposed in a housing;

an excitation arrangement
  which in operation sets the measuring tube into flexural vibrations and into torsional vibrations equal in frequency to the flexural vibrations, and
  first portions of which are fixed to the cantilever and second portions of which are fixed to the support frame;

a first sensor,
  a first and a second portion of which are fixed to the measuring tube and the support frame, respectively, approximately midway between the inlet end and the cantilever; and a second sensor,
  a first and a second portion of which are fixed to the measuring tube and the support frame, respectively, approximately midway between the outlet end and the cantilever.

U.S. Pat. No. 5,796,011, particularly in connection with FIG. 5, describes a Coriolis mass flow rate sensor designed to be installed in a pipe through which a fluid flows at least temporarily, and comprising:

a first measuring tube bent in a first plane symmetrically with respect to a first axis of symmetry;
a second measuring tube bent in a second plane symmetrically with respect to a second axis of symmetry,
  which measuring tubes are arranged parallel to each other and are of one-piece construction, and
  each of which measuring tubes has
    a straight inlet portion with an inlet axis lying in the first plane and the second plane, respectively,
    a straight outlet portion with an outlet axis aligned with the inlet axis,
    an inlet bend connected with the inlet portion,
    an outlet bend connected with the outlet portion, and
    a circular-arc-shaped vertex portion of minimum height connected with the inlet bend and outlet bend,
      which inlet portions and which outlet portions are connected in parallel in terms of fluid flow by means of an inlet manifold and an outlet manifold, respectively, and
      which manifolds are mounted in a support frame which forms part of a housing;

a first node plate rigidly connecting the two measuring tubes at a location
  where the inlet bend passes into die circular-arc-shaped vertex bend;

a second node plate rigidly connecting the two measuring tubes at a location
  where the outlet bend passes into the circular-arc-shaped vertex bend;

an excitation system
  which in operation causes the measuring tubes to vibrate as a tuning fork,
  a first portion of which Is fixed to the circulararc-shaped vertex bend of the first measuring tube in the area of the axis of symmetry of the first measuring tube, and
  a second portion of which is fixed to the circular-arc-shaped vertex bend of the second measuring tube in the area of the axis of symmetry of the second measuring tube;

a first sensor,
  a first portion of which is fixed to the first measuring tube and a second portion of which is fixed to the second measuring tube at respective locations where the respective inlet bend passes into the respective circular-arc-shaped vertex bend;

a second sensor,
   a first portion of which fixed to the first measuring tube and a second portion of which is fixed to the second measuring tube at respective locations
      where the respective outlet bend passes into the respective circular-arc-shaped vertex bend;
a feedthrough mounted in the support frame opposite the circular-arc-shaped vertex bends and containing several electric conductors; and
a printed-circuit board attached to the support frame and extending between the inlet manifold and outlet manifold and having conducting tracks
   via which leads of the excitation system and the sensors are connected to the conductors of the feedthrough.

To the above referred ensembles of features of the individual prior-art arrangements it should be added that a straight measuring tube or straight measuring tubes are preferably made of pure titanium, a high-titanium alloy, pure zirconium, or a high-zirconium alloy, since, compared with measuring tubes of stainless steel, which is suitable material for straight measuring tubes in principle, shorter overall lengths are obtained, and that a bent measuring tube or bent measuring tubes are preferably made of stainless steel, although titanium or zirconium or their alloys are suitable materials for such tubes as well.

The design principle of the Coriolis mass flow rate sensor according to U.S. Pat. No. 5,796,011 permits the use of only such circular-arc vertex bends which have a great radius of curvature, i.e., where the distance between the circular-arc vertex bend and the inlet/outlet axis is minimal as a function of the inside diameter and the wall thickness of the measuring tubes and of a permissible, temperature-range-induced mechanical stress. For distances between the vertex and the inlet/outlet axis that are greater than the minimum distance, however, particularly for distances greater than the minimum distance by an order of magnitude, the design principle of U.S. Pat. No. 5,796,011 is unsuitable.

Therefore, starting from the design principle U.S. Pat. No. 5,796,011, it is an object of the invention to provide a Coriolis mass flow rate/density/viscosity sensor in which the distance between the vertex of the vertex bend and the inlet/outlet axis can be virtually arbitrarily great. At the same time, high measurement accuracy, for example of the order of ±0.5%, is to be achievable, manufacturing costs are to be minimized as compared to those of prior-art mass flow rate sensors, mass flow rate/density sensors, or mass flow rate/density/viscosity sensors, and a shorter overall length is to be made possible.

To attain these objects, the invention provides a Coriolis mass flow rate/density/viscosity sensor designed to be installed in a pipe through which a fluid flows at least temporarily, and comprising:
   a first measuring tube bent to a V shape in a first plane symmetrically with respect to a first axis of symmetry;
   a second measuring tube bent to a V shape in a second plane symmetrically with respect to a second axis of symmetry,
      which measuring tubes are arranged parallel to each other and are each of one-piece construction, and each of which measuring tubes has
         a straight inlet portion with an inlet axis lying in the first plane and second plane, respectively,
         a straight outlet portion with an outlet axis lying in the first plane and second plane, respectively, and aligned with the inlet axis,
         an inlet bend connected with the inlet portion,
         an outlet bend connected with the outlet portion,
         a first straight tube portion connected with the inlet bend,
         a second straight tube portion connected with the outlet bend, and
         a vertex bend connected with the first and second straight tube portions,
            which inlet portions are fixed in an inlet manifold, which outlet portions are fixed in an outlet manifold, and
            which manifolds are mounted in a support frame which forms part of a housing;
   an excitation arrangement
      which in operation causes the measuring tubes to vibrate as a tuning fork,
      a first portion of which is fixed to the vertex bend of the first measuring tube in the area of the axis of symmetry of the first measuring tube, and
      a second portion of which is fixed to the vertex bend of the second measuring tube in the area of the axis of symmetry of the second measuring tube;
   a first velocity or displacement sensor,
      a first portion of which is fixed to the first straight tube portion of the first measuring tube, and
      a second portion of which is fixed to the first straight tube portion of the second measuring tube;
   a second velocity or displacement sensor, positioned symmetrically with respect to the axes of symmetry of the measuring tubes,
      a first portion of which is fixed to the second straight tube portion of the first measuring tube, and a second portion of which is fixed to the second straight tube portion of the second measuring tube;
   a feedthrough mounted in the support frame opposite the vertex bends and containing several electric conductors; and
   a printed-circuit board attached to the support frame and extending between the support frame and the vertex bends and having conducting tracks
      to which leads of the excitation system and of the velocity or displacement sensors are connected.

In a preferred embodiment of the invention, the measuring tubes
   are rigidly connected by a first node plate in the vicinity of a location
      where the respective inlet portion passes into the respective inlet bend,
   are rigidly connected by a second node plate in the vicinity of a location
      where the respective inlet bend passes into the respective first straight tube portion,
   are rigidly connected by a third node plate in the vicinity of a location
      where the respective outlet portion passes into the respective outlet bend, and
   are rigidly connected by a fourth node plate in the vicintiy of a location
      where the respective outlet bend passes into the respective second straight tube portion.

According to a first development of the invention and/or of the above preferred embodiment, electrodynamic velocity sensors are used and the excitation system is of the electrodynamic type.

According to a second development of the invention, which can also be used with the above preferred embodiment and/or the first development,
   the support frame is of one-piece construction and is made of stainless sheet steel of constant width and thickness having a front face and a rear face, comprises:

a plane inlet frame portion, which has the inlet manifold welded therein, a plane outlet frame portion, which has the outlet manifold welded therein, a plane feedthrough frame portion connecting the inlet frame portion and outlet frame portion and having the feedthrough mounted therein in a pressure-tight manner, a first plane extension frame portion extending from the inlet frame portion at an angle greater than 90°, a bent vertex frame portion passing into the first extension frame portion, and a second plane extension frame portion extending from the outlet frame portion at said angle and passing into the vertex frame portion; and the support frame is supplemented by a plane front sheet of stainless steel, which is welded to the front, and a plane rear sheet of the same steel, which is welded to the rear face, to form the housing.

According to a third development of the invention, which can also be used with the preferred embodiment and/or the first and/or second developments, the feedthrough comprises:

a flange attached to the support frame and having a hole;

the printed-circuit board, which is passed through a slot formed in the feedthrough frame portion and extends into the flange, with the printed-circuit board and the slot separated by a distance sufficient for electric isolation;

a disk of insulating material resting on the feedthrough frame portion and through which the printed-circuit board is passed; and an insulating compound filling a portion of the hole lying above the disk, the insulating compound having a thickness at least equal to the gap length specified for type of protection Ex-d as a function of gap width.

One advantage of the invention is that it permits the construction of Coriolis mass flow rate/density/viscosity sensors whose overall length, i.e., the length along the inlet/outlet axis, is considerably shorter than the overall length of the assembly according to U.S. Pat. No. 5,796,011. This is due to, among other things, the V shape of the measuring tube. A compact sensor with the desired measurement accuracy is obtained.

Furthermore, the design of the housing, which consists essentially of a support frame, a front steel sheet, and a rear steel sheet, contributes to the fact that the Coriolis sensor can be manufactured at very bw cost. Manufacturing costs are also kept low through the use of the printed-circuit board for the feedthrough, since the board provides a simple and low-cost electrical connection between the excitation system and the sensors on the one hand and evaluation electronics on the other.

BRIEF DESCRIPTION OF THE DRAWINGS

The invention will now be explained in more detail with reference to the accompanying drawings, which show a preferred embodiment of the invention. Corresponding components are designated by the same reference numerals throughout the various figures, but reference numerals are repeated in subsequent figures only if this appears appropriate. In the drawings.

DETAILED DESCRIPTION OF EXEMPLARY EMBODIMENTS

Figure 1:
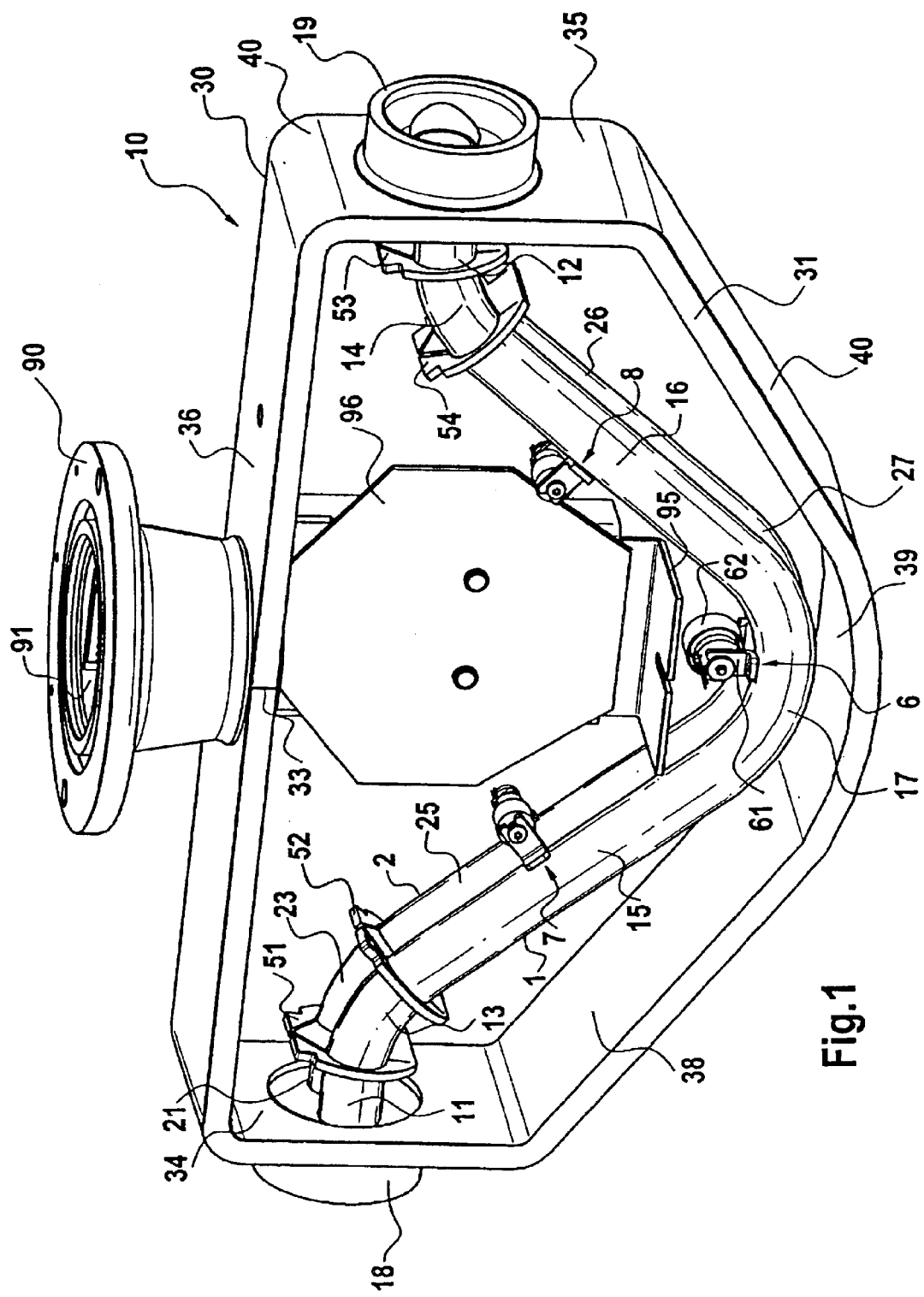
FIG. 1 is a perspective view showing mechanical details of a Coriolis sensor, with its housing not completed.

While the invention is susceptible to various modifications and alternative forms, exemplary embodiments thereof have been shown by way of example in the drawings and will herein be described in detail. It should be understood, however, that there is no intent to limit the invention to the particular forms desclosed, but on the contrary, the invention is to cover all modifications, equivalents, and alternatives falling within the spirit and scope of the invention as defined by the appended claims.

Figure 2:
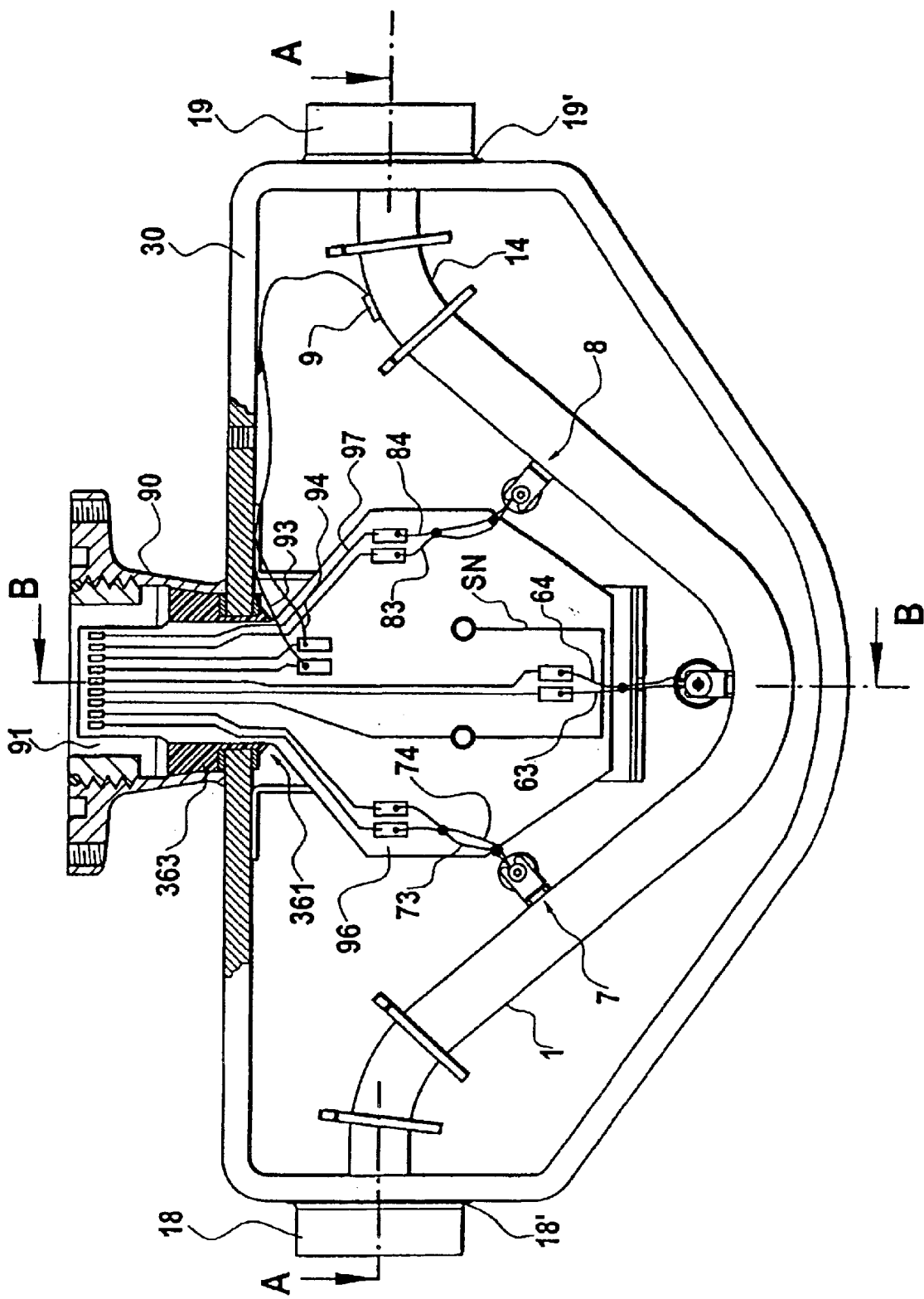
FIG. 2 is a front view of the Coriolis sensor of FIG. 1, again with its housing not completed, but with additional electrical details.

FIG. 1 is a perspective view showing only mechanical details of a Coriolis mass flow rate/density/viscosity sensor, referred to herein as a Coriolis sensor 10 for short, but with its housing not completed in order to more clearly show its internal construction, and FIG. 2 is a corresponding front view with additional electrical details.

Figure 4:
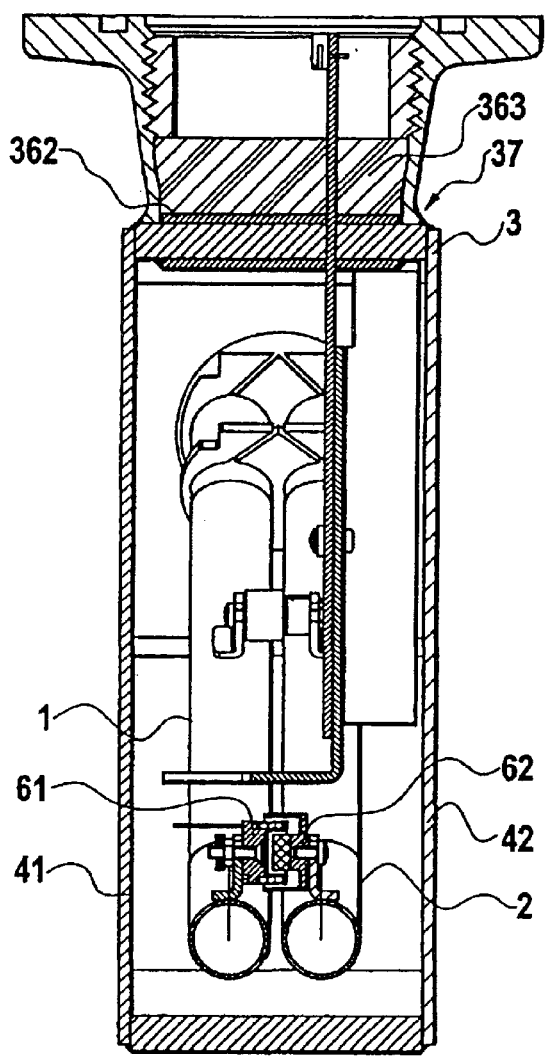
FIG. 4 is a section taken along line B—B of FIG. 2, showing the Coriolis sensor in a side view and again with the housing completed.
Figure 3:
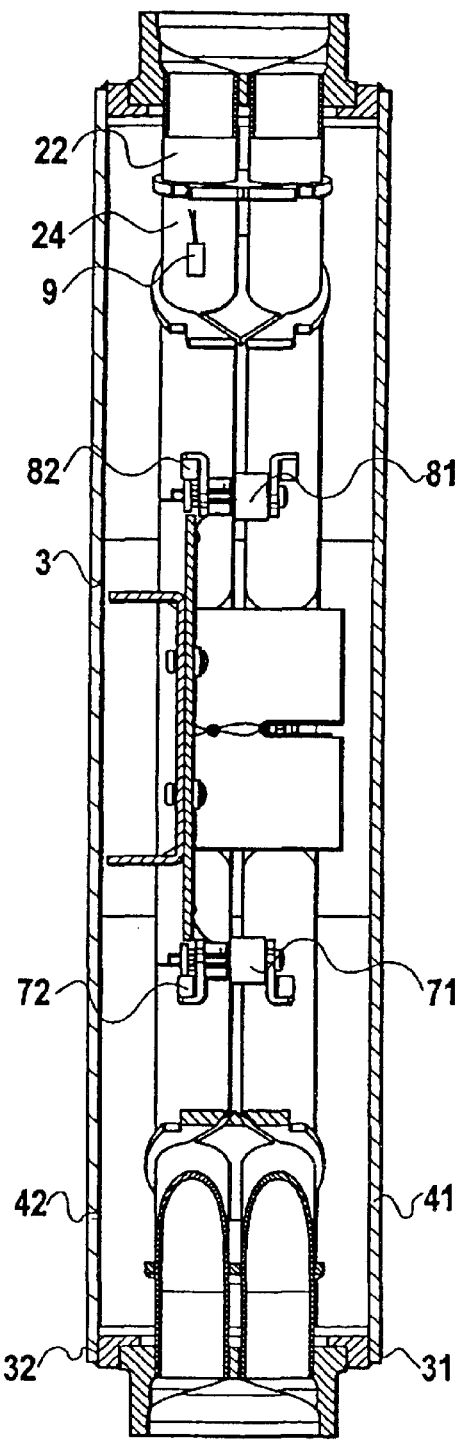
FIG. 3 is a section taken along line A—A of FIG. 2, showing the Coriolis sensor in a plan view, but with the housing completed.

FIGS. 3 and 4 are sectional views of FIG. 2 with the housing completed. Because of the representation chosen, a perspective FIG. 1 along with front, plan, and side views, in the following the figures are described not one after the other, but together.

Coriolis sensor 10 has a first V-shaped measuring tube 1, which is bent in a first plane symmetrically with respect to a first axis of symmetry. A second V-shaped measuring tube 2 is bent in a second plane symmetrically with with respect to a second axis of symmetry. Measuring tubes 1, 2 are arranged parallel to each other, and each of them is of one-piece construction.

Measuring tube 1 has a straight inlet portion 11 with an inlet axis lying in the first plane, and a straight outlet portion 12 with an outlet axis lying in the first plane and aligned with the inlet axis; a common axis is thus obtained, which will hereinafter be referred to as an inlet/outlet axis.

Measuring tube 2 has a straight inlet portion 21 with an inlet axis lying in the second plane, a straight outlet portion 22 (visible only in FIG. 3) with an outlet axis lying in the second plane and aligned with the inlet axis; this common axis, too, will hereinafter be referred to as an inlet/outlet axis.

Measuring tube 1 further has an inlet bend 13 connected with inlet portion 11, an outlet bend 14 connected with outlet portion 12, a first straight tube portion 15 connected with inlet bend 13, a second straight tube portion 16 connected with outlet bend 14, and a vertex bend 17 connected with the first and second straight tube portions 15, 16.

Measuring tube 2 further has an inlet bend 23 connected with inlet portion 21, and outlet bend 24 (visible only in FIG. 3) connected with outlet portion 22, a first straight tube portion 25 connected with inlet bend 23, a second straight tube portion 26 connected with outlet bend 24, and a vertex bend 27 connected with the straight tube portions 25, 26. In the embodiment shown, the curvature of the axis of vertex bend 17 and that of vertex bend 27 coreespond practically to the arc of a circle.

Inlet portions 11, 21 are fixed in an inlet manifold 18, and outlet portions 12, 22 are fixed in an outlet manifold 19. These manifolds 18, 19 are mounted in a support frame 30, which forms part of a housing 3 (visible only in FIGS. 3 and 4).

In the embodiment, measuring tubes 1, 2 and manifolds 18, 19 are made of stainless steel. Preferably, the stainless steel with the European material number 1.4539, corresponding to the American designation 904 L, is used for measuring tubes 1, 2, and the stainless steel with the European material number 1.4404, corresponding to the American designation 316 L, is used for manifolds 18, 19.

Coriolis sensor 10 is designed to be installed in a pipe through which a fluid to be measured flows at least temporarily. To that end, the manufacturer provides inlet and outlet manifolds 18, 19 with customized connection means, such as connections with an internal or external thread, flanges, or clamping devices as are commercially available, for example, under the registered trademark Triclamp.

Like measuring tubes 1, 2, support frame 30 is of one-piece construction. It was made from a flat bar of high-grade steel and of constant width and thickness by suitably bending the bar and welding its ends, see the joint 33, and it has a front face 31 and a rear face 32 (visible only in FIGS. 3 and 4).

Support frame 30 comprises a plane inlet frame portion 34, in which inlet manifold 18 is fixed by welding, and a plane outlet frame portion 35, in which outlet manifold 19 is fixed by welding, see in FIG. 2 the portions 18 and 19 protruding from support frame 30, with associated welds 18' and 19', respectively.

Support frame 30 further comprises a plane feedthrough frame portion 36, which connects inlet frame portion 34 and outlet frame portion 35, and in which a feedthrough 37 (visible only in FIG. 4) is fixed in a pressure-tight manner. Feedthrough frame portion 36 forms respective right angles with inlet and outlet frame portions 34, 35.

Support frame 30 further comprises a first plane extension portion 38, which extends from inlet frame portion 34 at an angle greater than 90°, in the embodiment approximately 120°. Support frame 30 finally comprises a bent vertex portion 39, which passes into extension portion 38, and a second plane extension portion 40, which extends from outlet frame portion 35 at the above-mentioned angle and passes into vertex portion 39.

Support frame 30 is supplemented by a plane front sheet 41 of stainless steel welded to front face 31 and a preferably plane rear sheet 42 of the same steel welded to rear face 32 to form the housing 3, 50 that the latter is pressure-tight. Front and rear sheets 41, 42 can only be seen in FIGS. 3 and 4. In the embodiment, the steel preferably used for housing 3 is the stainless steel with the European material number 1.4301, which corresponds to the American designation 304.

The preferably plane front and rear sheets 41, 42 result in a higher stiffness of housing 3 under compressive stress in the direction of the inlet/outlet axis than if these sheets were provided with longitudinal crimps. Measuring tubes 1, 2 are rigidly connected by a first node plate 51 in the vicinity of a location where the respective inlet portion 11, 21 passes into the respective inlet bend 13, 23, and by a second mode plate 52 in the vicinity of a location where the respective inlet bend 13, 23 passes into the respective first straight tube portion 15, 25.

Furthermore, measuring tubes 1, 2 are rigidly connected by a third node plate 53 in the vicinity of a location where the respective outlet portion 12, 22 passes into the respective outlet bend 14, 24, and by a fourth node plate 54 in the vicinity of a location where the respective outlet bend 14, 24 passes into the respective second straight tube portion 16, 26.

The four node plates 51, 52, 53, 54 are preferably thin plates of stainless steel, particularly of the same steel as that used for housing 3. These plates are provided with holes whose diameters correspond to the outside diameters of measuring tubes 1, 2, and with slots, so that they can be first clamped onto and then brazed to measuring tubes 1, 2, with the slots being brazed together as well, so that the plates are seated on measuring tubes 1, 2 unslotted as node plates.

In operation, an excitation system 6 vibrates measuring tubes 1, 2 as a tuning fork at a frequency equal or close to the mechanical resonance frequency of the vibrating system formed by measuring tubes 1, 2. This vibration frequency, as is well known, is dependent on the density of the fluid flowing through measuring tubes 1, 2. Therefore, the density of the fluid can be determined from the vibration frequency.

A first portion 61 of excitation system 6 is fixed to vertex bend 17 of measuring tube 1 in the area of the above-mentioned axis of symmetry of this tube, and a second portion 62 of excitation system 6 is fixed to vertex bend 27 of measuring tube 2 in the area of the above-mentioned axis of symmetry of this tube, see FIG. 4.

In the embodiment shown in the figures, excitation system 6 is an electrodynamic shaker, i.e., portion 61 is a coil and portion 62 a permanent magnet that cooperates with the coil by riding therein.

Excitation system 6 is supplied with AC power from a driver circuit (not shown), which may, for instance, be a PLL circuit that continuously adjusts the instantaneous resonance frequency of the vibrating system of measuring tubes 1, 2. Such a PLL circuit is disclosed in U.S. Pat. No. 4,801,897, the disclosure of which is hereby incorporated by reference.

A first velocity or displacement sensor 7 and a second velocity or displacement sensor 8, which are mounted on measuring tubes 1, 2 symmetrically with respect to the aforementioned axes of symmetry, produce measurement signals from which the mass flow rate, the density, and, if desired, the viscosity of the fluid can be determined.

A first portion 71 of velocity or displacement sensor 7 is fixed to the straight portion 15 of measuring tube 1, and a second portion iZ is fixed to the straight portion 25 of measuring tube 2, see FIG. 3. A first portion 81 of velocity or displacement sensor 8 is fixed to the straight portion 16 of measuring tube 1, and a second portion 82 is fixed to the straight portion 26 of measuring tube 2, see FIG. 3.

In the embodiment shown in the figures, velocity or displacement sensors 7, 8 are preferably electrodynamic velocity sensors; thus, each of portions 71, 81 is a coil, and each of portion 72, 82 is a permanent magnet that can ride in the associated coil.

As already briefly mentioned above, feedthrough 37, which contains several electric conductors, is mounted in support frame 30 opposite vertex bends 17, 27, and thus opposite vertex frame portion 39, particularly in a pressure-tight manner. To that end, a flange 90 is attached to support frame 30; preferably, flange 90 is welded to support frame 30. Flange 90 has a hole 91, so that feedthrough 37 is accessible from outside housing 3.

Feedthrough 37 comprises a printed-circuit board 96, which is fastened to support frame 30 by means of an angled support plate 95 and which extends between support frame 30 and the vertex bends toward the latter. Printed-circuit board 96 has conducting tracks formed thereon, cf. conducting track 97, which are only visible in FIG. 2.

Connected to respective ones of these conducting tracks are leads 63, 64 of excitation system 6, leads 73, 74 of velocity sensor 7, leads 83, 84 of velocity sensor 8, and leads 93, 94 of a temperature sensor 9, which are thus also connectect to the individual conductors ot feedthrough 37. Leads 63, 64, 73, 74, 83, 84, 93, 94 can only be seen in FIG. 2. In addition, a conducting track SN to ground is provided on the printed-circuit board, which is mechanically and, thus, electrically attached to the metallic support plate 95.

In the embodiment shown, temperature sensor 9 (visible only in FIGS. 2 and 3) is attached to outlet bend 14 of measuring tube 1, for instance with adhesive, and is preferably a platinum resistance element. As mentioned above, it serves to measure the current temperature of the fluid. Temperature sensor 9 may also be positioned at any other suitable location of measuring tubes 1, 2.

Feedthrough 37 further comprises a slot 361 formed in feedthrough frame portion 36, through which the printed-circuit board 96 is passed and extends into flange 90, with a distance sufficient for electrical isolation being maintained between printed circuit board 96 and slot 361.

Furthermore, printed-circuit board 96 is passed through a disk 362 of insulating material resting on feedthrough frame portion 36. An insulating compound 363 completely fills a portion of hole 91 lying above disk 362, and may also have penetrated into the space between printed-circuit board 96 and the internal wall of slot 363.

The thickness of insulating compound 363 in the direction of the open end of hole 91 is at least equal to the gap length required for type of protection Ex-d according to European Standard EN 50014 and EN 50018 as a function of gap width, the disclosures of which are hereby incorporated by reference. These standards correspond to comparable standards of other countries.

As Coriolis sensor 10 has to be equipped with associated control and evaluation electronics to obtain an operational Coriolis mass flow rate/density/viscosity meter, a housing (not shown) for those control and evaluation electronics or a terminal arrangement (not shown) for a cable running to a control and evaluation electronics housing remote from the Coriolis sensor is screwed to flange 90.

While the invention has been illustrated and described in detail in the drawing and foregoing description, such illustration and description is to be considered as exemplary and not restrictive in character, it beeing understood that only exemplary embodiments have been shown and described and that all changes and modifications that come within the spirit of the invention are desired to be protected.

What is claimed is:

1. Coriolis mass flow sensor for measuring a fluid flowing through a pipe, said sensor comprising:
   a first tube for conducting the fluid to be measured, said first tube having a single substantially V-shaped tube segment with an inlet-side straight tube portion and an outlet-side straight tube portion, said straight tube portions being in connection via a vertex bend portion of said first tube segment, said V-shaped tube segment being coupled to the pipe during operation;
   a second tube having a single substantially V-shaped tube segment with an inlet-side straight portion and an outlet-side straight portion, said straight portions being in connection via a vertex bend portion of said second tube segment;
   wherein said first and said second tubes are coupled mechanically with each other at an inlet-side location and an outlet-side location, respectively;
   an excitation arrangement coupled to said first and said second tubes for vibrating said first and said second tubes; and
   a sensor arrangement coupled to said first and said second tubes for detecting inlet-side and outlet-side vibrations of at least one of the tubes.

2. The Coriolis mass flow sensor as claimed in claim 1 wherein the V-shaped tube segment being coupled to the pipe via an inlet-side tube segment and an outlet-side tube segment, respectively.

3. The Coriolis mass flow sensor as claimed in claim 1 wherein the inlet-side straight portion of said tube segment and the outlet-side straight portion of said tube segment are aligned to each other.

4. The Coriolis mass flow sensor as claimed in claim 1 wherein the second tube having an inlet-side tube segment being connected with the V-shaped tube segment via whose inlet-side straight tube portion and an outlet-side tube segment being connected with the V-shaped tube segment via whose outlet-side straight tube portion.

5. The Coriolis mass flow sensor as claimed in claim 4 wherein the first and second tubes are shaped in an identical manner.

6. The Coriolis mass flow sensor as claimed in claim 4 wherein the first node plate is affixed to said inlet-side tube segments of the first and second tube sand the second node plate is affixed to said outlet-side tube segments of the first and second tubes.

7. The Coriolis mass flow sensor as claimed in claim 4 comprising an inlet-side manifold fixed to said inlet-side tube segments of the first and second tubes and an outlet-side manifold fixed to said outlet-side tube segments of the first and second tubes.

8. The Coriolis mass flow sensor as claimed in claim 7, wherein the support frame is affixed to the inlet-side and the outlet-side manifolds.

9. The Coriolis mass flow sensor as claimed in claim 7 further comprising a support frame, said support frame being coupled to said inlet-side tube segment and said outlet-side tube segment of the first tube, wherein the support frame is affixed to the inlet-side and the outlet-side manifolds.

10. The Coriolis mass flow sensor as claimed in claim 1 comprising a first node plate affixed to each of the tubes at said inlet-side location and a second node plate affixed to each of the tubes at said outlet-side location.

11. The Coriolis mass flow sensor as claimed in claim 10 wherein the first node plate is affixed to said inlet-side straight tube portions of the first and the second tubes and the second node plate is affixed to said outlet-side straight tube portions of the first and the second tubes.

12. The Coriolis mass flow sensor as claimed in claim 10 wherein the first node plate is affixed to said inlet-side tube segments of the first and second tube sand the second node plate is affixed to said outlet-side tube segments of the first and second tubes.

13. The Coriolis mass flow sensor as claimed in claim 12 wherein the support frame is affixed to the inlet-side and the outlet-side manifolds.

14. The Coriolis mass flow sensor as claimed in claim 1 comprising a support frame, said support frame being coupled to said inlet-side tube segment and said outlet-side tube segment of the first tube.

15. The Coriolis mass flow sensor as claimed in claim 1 wherein the V-shaped tube segment of said first tube is coupled to the pipe via an inlet-side tube segment and an outlet-side tube segment, respectively.

16. The Coriolis mass flow sensor as claimed in claim 1 further comprising an inlet-side manifold connected with the first and second tubes and an outlet-side manifold connected with said first and second tubes.

17. The Coriolis mass flow sensor as claimed in claim 16 further comprising a support frame, said support frame being coupled to said first and second tubes, wherein the support frame is affixed to the inlet-side and the outlet-side manifolds.

18. The Coriolis mass flow sensor as claimed in ciaim 16 further comprising a housing, said housing being coupled to the first and second tubes via said inlet-side and outlet-side manifolds.

19. The Coriolis mass flow sensor as claimed in claim 1 wherein the V-shaped tube segment of said first tube is coupled to the pipe via an inlet-side tube segment and an outlet-side tube segment, respectively, and wherein the second tube has an inlet-side tube segment being connected with the V-shaped tube segment via whose inlet-side straight tube portion and an outlet-side tube segment are connected with the V-shaped tube segment via whose outlet-side straight tube portion.

20. The Coriolis mass flow sensor as claimed in claim 1 comprising a first node plate affixed to the first and the second tubes at said inlet-side location and a second node plate affixed to the first and the second tubes at said outlet-side location.

21. The Coriolis mass flow sensor as claimed in claim 1 further comprising an inlet-side manifold connected with the first and second tubes and an outlet-side manifold connected with said first and second tubes, wherein the first and second tubes are coupled to the pipe via said inlet-side and outlet-side manifolds during operation.

22. The Coriolis mass flow sensor as claimed in claim 1 wherein each of the inlet-side tube segment and an outlet-side tube segment of the first tube comprises a bend portion.

23. The Coriolis mass flow sensor as claimed in claim 22, wherein each of the inlet-side tube segment and an outlet-side tube segment of the first tube comprises a straight portion.

24. The Coriolis mass flow sensor as claimed in claim 23 wherein the straight portion of said inlet-side tube segment and a straight portion of said outlet-side tube segment are aligned to each other.

25. The Coriolis mass flow sensor as claimed in claim 1 wherein the first and second tubes are shaped in an identical manner.

26. The Coriolis mass flow sensor as claimed in claim 1 wherein a curvature of each of said vertex bend portions corresponds to the arc of a circle.

27. The Coriolis mass flow sensor as claimed in claim 26 wherein the first and second tubes are shaped in an identical manner.

28. The Coriolis mass flow sensor as claimed in claim 1 further comprising a temperature sensor attached to said first tube.

29. The Coriolis mass flow sensor as claimed in claim 1 further comprising a support, wherein the first and second flow tubes are mounted within said support.

30. The Coriolis mass flow sensor as claimed in claim 29 wherein the support is coupled to said inlet-side tube segment and said outlet-side tube segment of the first tube.

31. The Coriolis mass flow sensor as claimed in claim 30 further comprising an inlet-side manifold connected with the first and second tubes and an outlet-side manifold connected with said first and second tubes, wherein the first and second tubes are coupled to the pipe via said inlet-side and said outlet-side manifolds during operation.

32. The Coriolis mass flow sensor as claimed in claim 30 wherein the support is affixed to the inlet-side and the outlet-side manifolds.

33. The Coriolis mass flow sensor as claimed in claim 32 further comprising a temperature sensor attached to said first tube.

34. The Coriolis mass flow sensor as claimed in claim 1 further comprising a support frame, wherein the first and second flow tubes are disposed within said support frame.

35. The Coriolis mass flow sensor as claimed in claim 1 wherein the excitation arrangement is an electrodynamic shaker.

36. The Coriolis mass flow sensor as claimed in claim 1 wherein the sensor arrangement comprises electrodynamic velocity sensors mounted on said first and second tubes.

37. A support frame of a Coriolis mass flow sensor for measuring a fluid flowing through a pipe, said Coriolis mass flow sensor one including two bent measuring tube for conducting the fluid to be measured, said measuring tubes being disposed within the support frame, said support frame comprising:

a substantially plane inlet-side frame portion and a substantially plane outlet-side frame portion, both frame portions being disposed opposite to each other;

a substantially plane feedthrough frame portion having a feedthrough and connecting said inlet-side frame portion and said outlet-side frame portion with each other; and a bent vertex frame portion being connected to said inlet-side frame portion and said outlet-side frame portion and being disposed opposite to said feedthrough frame portion;

wherein the two measuring tubes are fixed to said inlet-side and said outlet-side frame portions.

38. The support frame as claimed in claim 37 wherein each one of the inlet-side frame portion, the outlet-side frame portion, the feedthrough frame portion, and the bent vertex frame portion having the same width.

39. The support frame as claimed in claim 37 wherein each one of the inlet-side frame portion, the outlet-side frame portion, the feedthrough frame portion, and the bent vertex frame portion having the same thickness.

40. The support frame as claimed in claim 37 wherein an inlet-side manifold is affixed to the inlet-side frame portion and an outlet-side manifold is affixed to the outlet-side frame portion, and wherein each one of a first bent measuring tube and a second bent measuring tube each being connected with said manifolds.

41. The support frame as claimed in claim 37 being supplemented by a front sheet and a rear sheet, said front sheet being affixed to the support frame at a first face of the support frame and said rear sheet being affixed to the support frame at a second face of the support frame.

42. A Coriolis mass flow sensor for measuring a fluid flowing through a pipe, said sensor comprising:

a first tube for conducting the fluid to be measured, said first tube including a single substantially V-shaped tube segment with an inlet-side straight tube portion and an outlet-side straight tube portion, said straight tube portions being in connection via a vertex bend portion of said first tube segment, said V-shaped tube segment being coupled to the pipe during operation;

a second tube including a single substantially V-shaped tube segment with an inlet-side straight portion and an outlet-side straight portion, said straight portions being in connection via a vertex bend portion of said second tube segment, and said first and said second tubes being coupled mechanically with each other at an inlet-side location and an outlet-side location, respectively;

an excitation system for vibrating said first and said second tubes; and a sensor arrangement for detecting inlet-side and outlet-side vibrations of at least one of the tubes.

43. The Coriolis mass flow sensor as claimed in claim 42 wherein a curvature of each of said vertex bend portions corresponds to the arc of a circle.

44. The Coriolis mass flow sensor as claimed in claim 42 wherein the first tube is bent symmetrically with respect to a first axis of symmetry and the second tube is bent symmetrically with respect to a second axis of symmetry.

45. The Coriolis mass flow sensor as claimed in claim 44 wherein a curvature of each of said vertex bend portions corresponds to the arc of a circle.

46. The Coriolis mass flow sensor as claimed in claim 42 wherein the excitation system includes a coil fixed to said vertex bend portion of the first tube and a magnet fixed to said vertex bend portion of the second tube.

47. The Coriolis mass flow sensor as claimed in claim 46 wherein the first tube is bent symmetrically with respect to a first axis of symmetry and the second tube is bent symmetrically with respect to a second axis of symmetry, and wherein the coil of the excitation system is fixed to said vertex bend portion in an area of said first axis of symmetry and wherein the magnet is fixed to said vertex bend portion in an area of said second axis of symmetry.

48. The Coriolis mass flow sensor as claimed in claim 47 wherein a curvature of each of said vertex bend portions corresponds to the arc of a circle.

49. The Coriolis mass flow sensor as claimed in claim 46 wherein the excitation arrangement is an electrodynamic shaker.

50. The Coriolis mass flow sensor as claimed in claim 49 wherein the sensor arrangement comprises electrodynamic velocity sensors mounted on said first and second cubes.

51. The Coriolis mass flow sensor as claimed in claim 49 further comprising a temperature sensor attached to said first tube, wherein a lead of said temperature sensor is connected to one of said conducting tracks printed-circuit board.

52. The Coriolis mass flow sensor as claimed in claim 42 further comprising:

an inlet-side manifold connected with the first and second tubes and an outlet-side manifold connected with said first and second tubes, and a housing being coupled to the first and second tubes via said inlet-side and outlet-side manifolds.

53. The Coriolis mass flow sensor as claimed in claim 42 further comprising:

an inlet-side manifold connected with the first and second tubes and an outlet-side manifold connected with said first and second tubes, and a support being coupled to the first and second tubes via said inlet-side and outlet-side manifolds.

54. The Coriolis mass flow sensor as claimed in claim 42 further comprising a temperature sensor attached to said first tube.

55. A Coriolis mass flow sensor for measuring a fluid flowing through a pipe, said sensor comprising:

a first tube for conducting the fluid to be measured and a second tube, said first and said second tubes coupled mechanically with each other at an inlet-side location and an outlet-side location, respectively, and, said first tube being coupled to the pipe during operation;

a support coupled with said first flow tube;

an excitation arrangement coupled to said first and said second tubes for vibrating said first and said second tubes;

a sensor arrangement coupled to said first and said second tubes for detecting inlet-side and outlet-side vibrations of at least one of the tubes, and a printed-circuit board being attached to the support that it extends between the support and said first and second flow tubes,
wherein the printed-circuit board has conducting tracks to which leads of the excitation arrangement and sensor arrangement are connected.

56. The Coriolis mass flow sensor as claimed in claim 55 further comprising a flange attached to the support, wherein the printed-circuit board extends into said flange.

57. The Coriolis mass flow sensor as claimed in claim 56 wherein the flange is filled with an insulating compound.

58. The Coriolis mass flow sensor as claimed in claim 56 wherein a space between the flange and said printed-circuit board is filled with an insulating compound.

59. The Coriolis mass flow sensor as claimed in claim 58 wherein the printed-circuit board is a part of an electrical feedthrough mounted in the support opposite the vertex bend portions of the first and second flow tubes.

60. The Coriolis mass flow sensor as claimed in claim 55 wherein each of the first and second tubes comprises a tube segment comprises a vertex bend portion, and wherein the printed-circuit board extends between the support and said vertex bend portions of the first and second flow tubes.

61. The Coriolis mass flow sensor as claimed in claim 60 wherein the tube segment of said first tube is substantially V-shaped and includes an inlet-side straight tube portion and an outlet-side portion, said straight tube portions being in connection via said vertex bend portion of the first tube, and wherein the tube segment of said second tube is substantially V-shaped and includes an inlet-side straight portion and an outlet-side straight portion, said straight portions being in connection via said vertex bend portion of the second tube.

* * * * *